(12) United States Patent
Sakata

(10) Patent No.: US 8,323,212 B2
(45) Date of Patent: Dec. 4, 2012

(54) ATTACHMENT FOR BODY FLUID SAMPLING DEVICE AND METHOD OF MAKING THE SAME

(75) Inventor: Tetsuya Sakata, Kyoyo (JP)

(73) Assignee: ARKRAY, Inc., Kyoto-shi (JP)

( * ) Notice: Subject to any disclaimer, the term of this patent is extended or adjusted under 35 U.S.C. 154(b) by 0 days.

(21) Appl. No.: 10/485,594

(22) PCT Filed: Aug. 2, 2002

(86) PCT No.: PCT/JP02/07934
§ 371 (c)(1),
(2), (4) Date: Feb. 2, 2004

(87) PCT Pub. No.: WO03/013356
PCT Pub. Date: Feb. 20, 2003

(65) Prior Publication Data
US 2004/0209350 A1 Oct. 21, 2004

(30) Foreign Application Priority Data
Aug. 3, 2001 (JP) ................................ 2001-237085

(51) Int. Cl.
*A61B 5/00* (2006.01)
(52) U.S. Cl. ...................................................... 600/573
(58) Field of Classification Search .................. 600/573, 600/583, 584, 576, 345; 606/181, 182
See application file for complete search history.

(56) References Cited

U.S. PATENT DOCUMENTS

| | | | |
|---|---|---|---|
| 6,099,484 A * | 8/2000 | Douglas et al. | 600/583 |
| 6,306,104 B1 * | 10/2001 | Cunningham et al. | 600/573 |
| 6,315,738 B1 * | 11/2001 | Nishikawa et al. | 600/583 |
| 6,540,762 B1 * | 4/2003 | Bertling | 606/182 |
| 6,766,817 B2 | 7/2004 | Da Silva | |
| 6,849,052 B2 * | 2/2005 | Uchigaki et al. | 600/584 |
| 7,025,774 B2 * | 4/2006 | Freeman et al. | 606/181 |
| 7,247,144 B2 * | 7/2007 | Douglas et al. | 600/583 |
| 7,378,007 B2 * | 5/2008 | Moerman et al. | 204/403.03 |
| 2002/0040230 A1 * | 4/2002 | Kuhr et al. | 606/181 |

FOREIGN PATENT DOCUMENTS

| | | | |
|---|---|---|---|
| JP | 5-95938 | | 4/1993 |
| JP | 9-108202 | | 4/1997 |
| JP | 2000-231 | | 1/2000 |
| JP | 2000-000231 | * | 7/2000 |
| JP | 2000-245717 | | 9/2000 |

* cited by examiner

*Primary Examiner* — Jeffrey G Hoekstra
*Assistant Examiner* — Fangemonique Smith
(74) *Attorney, Agent, or Firm* — Fox Rothschild LLP

(57) ABSTRACT

The present invention relates to an attachment (X) for body fluid sampling device, comprising: a lancing member (21) including a lancing needle (28); an analyzing implement (5) for obtaining information on a target component in body fluid; and an attachment main body (1) holding the lancing member (21) and the analyzing implement (5). The attachment main body (X) includes a movable member (3) movable with the analyzing implement (5) longitudinally of the lancing needle (28). The attachment main body (1) includes for example, a holder (2) for holding the lancing member (21). The holder (2) has an inner space (22) for movement of the lancing needle (28). The lancing needle (28) is held preferably as sealed in the inner space (22).

8 Claims, 11 Drawing Sheets

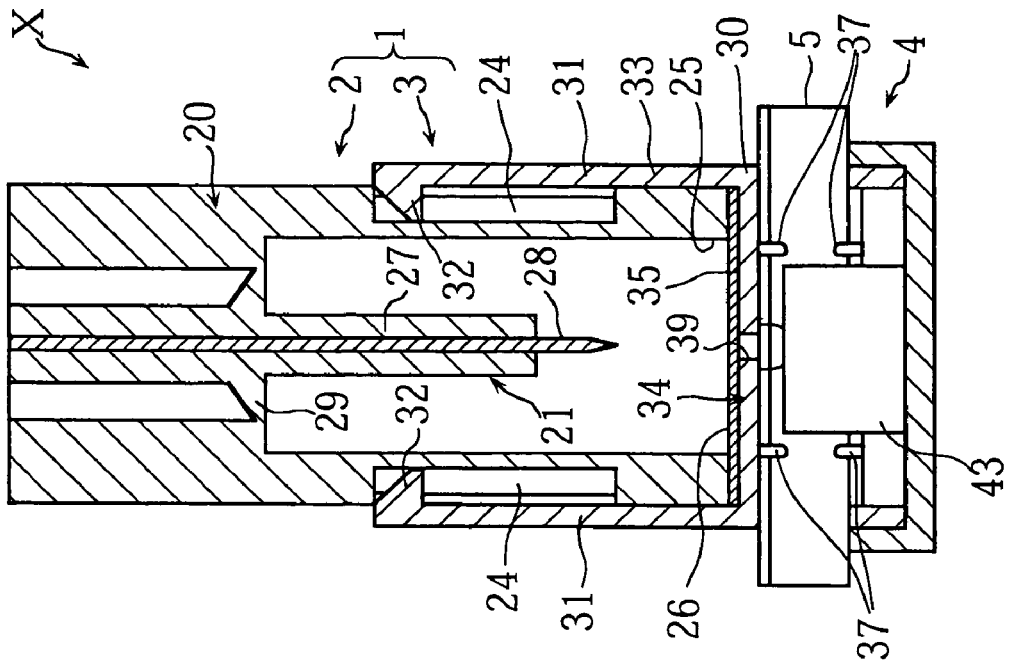
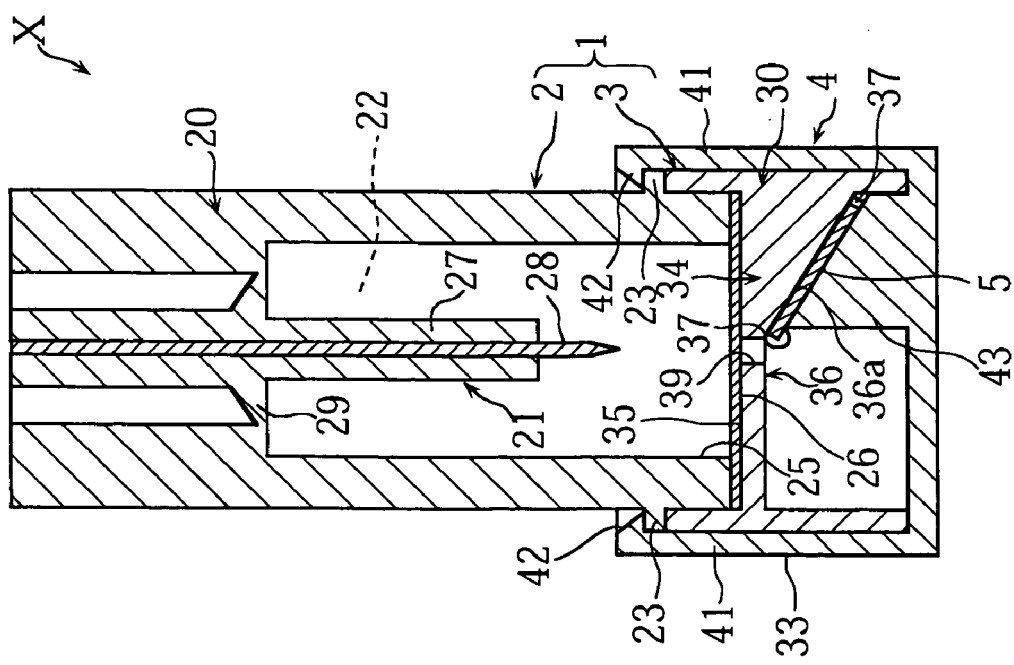

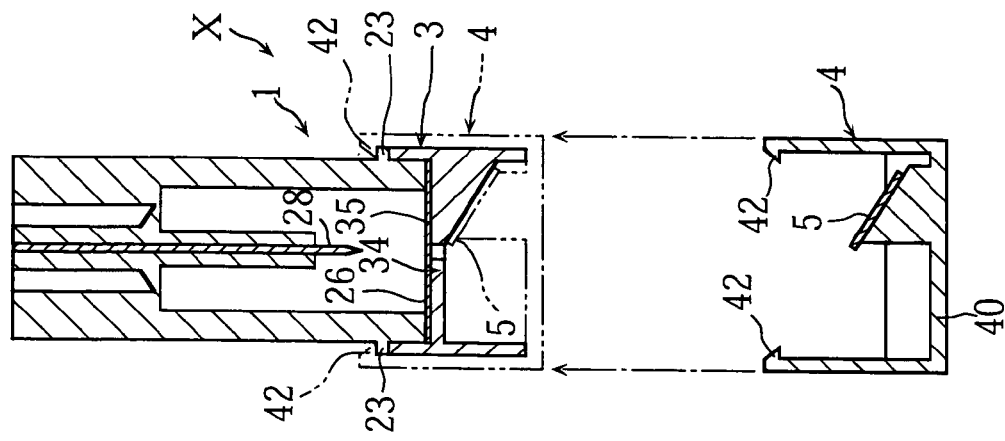
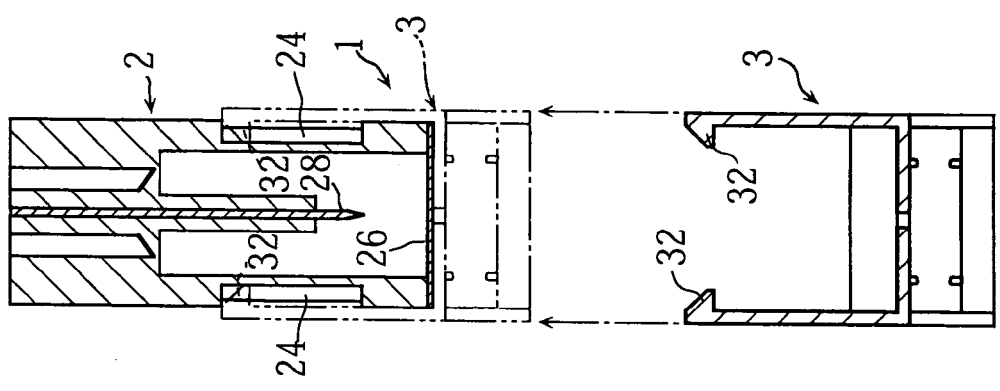
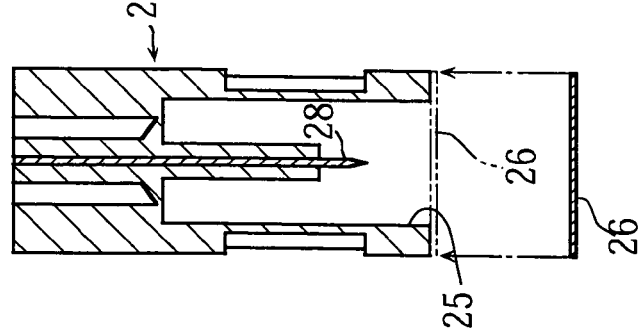

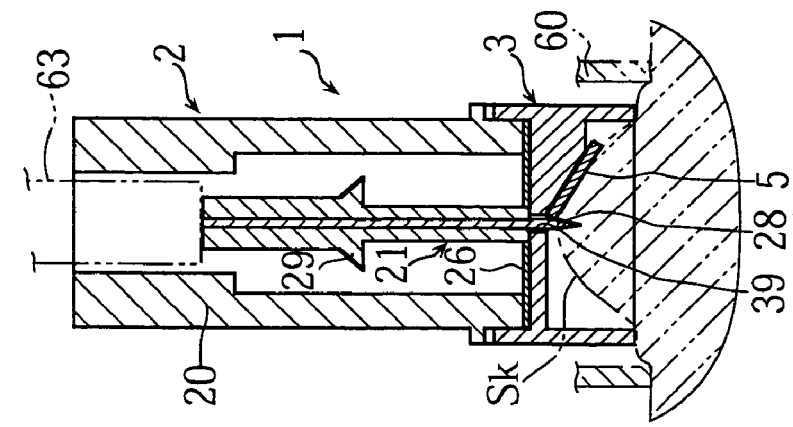
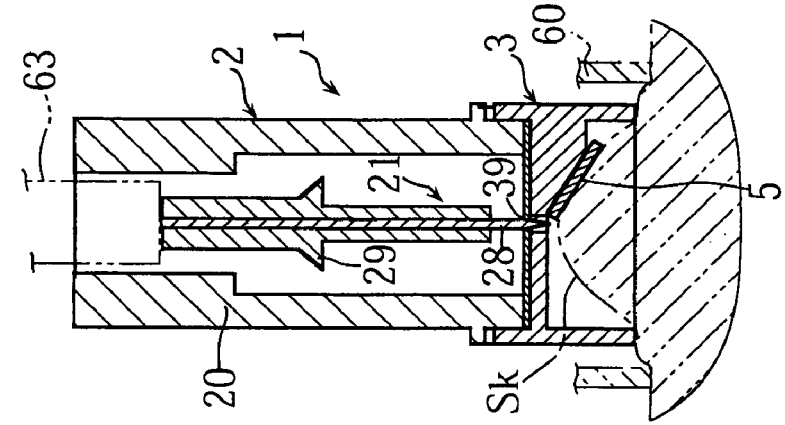
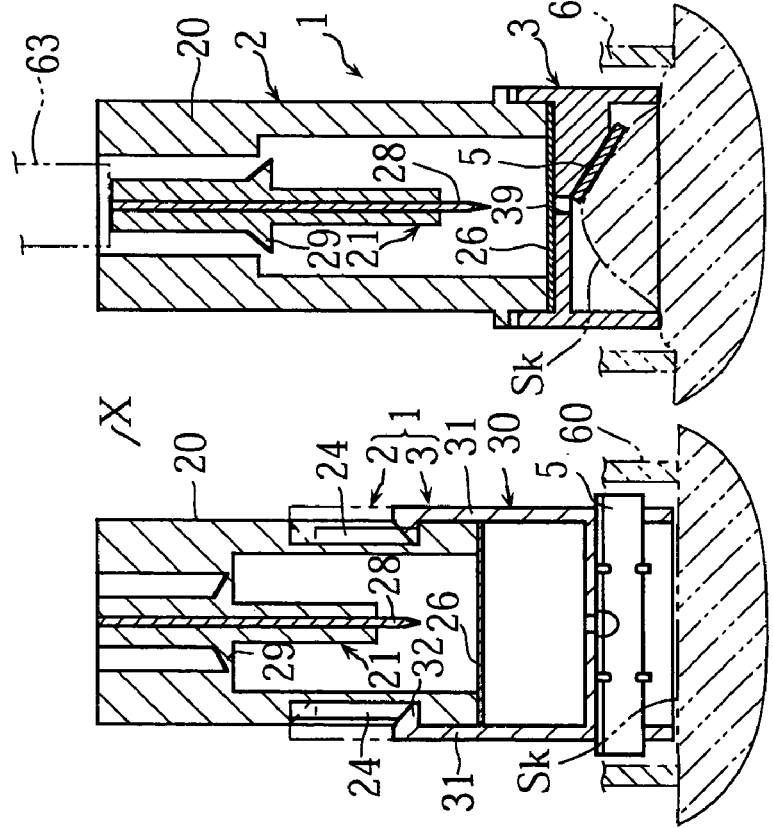

ATTACHMENT FOR BODY FLUID SAMPLING DEVICE AND METHOD OF MAKING THE SAME

TECHNICAL FIELD

The present invention relates to an attachment to a body fluid sampling device, and a method of making the same. In particular, the present invention relates to an attachment suitable to a body fluid sampling device capable of measuring the concentration of a target component.

BACKGROUND ART

When treating diabetes, it is important to control the patient's blood sugar level within the normal range, and so it is important that the patient has a control on his own blood sugar level. Especially for insulin-dependent patients, it is essential to check their blood sugar level regularly in their daily life in order to maintain the blood sugar level within the normal range. Since it is inconvenient to make frequent visit to a medical institute for the blood sugar measurement, portable blood sugar level testers are used so that the blood sugar level can be measured without the burden of visiting medical institutes.

An example of the portable blood sugar level tester is shown in FIG. 12 of the present application. This blood sugar level tester 8 uses an attachment 7. The attachment 7 includes a main body 70, which includes, integrally therewith, a lancing member 71 and a biosensor 72. The main body 70 has a housing space 73 for housing the lancing member 71. The housing space 73 has an opening 74, which is closed by the biosensor 72. The biosensor 72 provides an enzyme reaction field, and includes a layer of reagent containing an enzyme and an electron transfer material. The biosensor 72 is formed with a through hole for insertion of a lancing member 75 of the lancing member 71.

If the blood has to be sampled from a region which does not bleed easily, the blood sugar level tester 8 can be used to massage the target area Sk for improved blood flow, or the blood sugar level tester 8 can be used to press the target area Sk. Instead, the area may be sucked to cause blood congestion, or treated in different ways to promote bleeding from the target area Sk. In these actions, the target area Sk tends to bulge as shown in an imaginary line in the drawing, yet if the biosensor 72 is fixed on, the target area Sk is pressed onto the biosensor 72, and thus the target area Sk cannot bulge, leading to insufficient bleeding. If bleeding is insufficient, the biosensor cannot be supplied with a sufficient amount of blood necessary for the blood sugar level measurement, which can lead to an unacceptably large error in the measurement, or a process error in measuring steps. On the contrary, some parts of the human body may not bulge very much, and bulging of the skin varies from person to person. Under these conditions, there can be a case where the biosensor does not touch the skin at the time of lancing.

According to the attachment 7, the lancing needle 75 is exposed whether or not the biosensor 72 is integrated therewith. However, in view of sanitation on the lancing needle 75, the lancing needle 75 needs to be sterilized, and in order to prevent contamination after the sterilization, the lancing needle 75 must be sterilized as sealed in a space, and the sealing must be maintained till the time of use. Now, in order for the lancing needle 75 to be kept appropriately sterilized, the attachment 7 must be sealed with an aluminum laminate seal for example while the lancing member 71 and the biosensor 72 must be integrated into the main body 70. This is not possible for the attachment 7 in FIG. 12. Specifically, the lancing needle 75 cannot be sterilized separately from the biosensor 72 or from the enzyme contained in the biosensor 72.

The sterilization of the lancing needle 75 is made with gamma rays for example. Existence of an enzyme during the sterilization process, therefore, means that the enzyme will be destroyed or enzyme activity will be reduced. If such happens, a longer time will be required for the measurement, or the measured concentration can be lower than real, and in fact it becomes impossible to make appropriate measurement.

There is another problem: If the electron transfer material is provided by potassium ferricyanide, the gamma ray radiation reduces the potassium ferricyanide to potassium ferrocyanide. This is problematic if an amperometric method is used in the measurement of oxidation current, because part of the electron transfer material in the chemically reduced state is derived by the gamma ray radiation at the time of sterilization while the rest being derived from the enzyme reaction. Accordingly, when the electron transfer material in the chemically reduced state is oxidized by a voltage, a measured value of the oxidation current will be greater, which will give a concentration measurement higher than the real value, i.e. measuring accuracy will be low.

DISCLOSURE OF THE INVENTION

An object of the present invention is to provide an attachment which does not hinder operations for promoted bleeding from a point of lancing, clears problems associated with sterilization of the lancing needle, and is capable of performing appropriate measurement of concentration.

A first aspect of the present invention provides an attachment for body fluid sampling device, comprising: a lancing member including a lancing needle; an analyzing implement for obtaining information on a target component in body fluid; and an attachment main body holding the lancing member and the analyzing implement. The attachment main body includes a movable member movable with the analyzing implement longitudinally of the lancing needle.

The attachment main body includes, for example, a holder for holding the lancing member. In this case, the holder has an inner space for movement of the lancing member, and the lancing needle is held as sealed in the inner space.

The holder includes, for example, an opening for the inner space to communicate with outside. In this case, the inner space is sealed by a seal on the opening. Alternatively, the sealing of the inner space may be achieved by closing the opening with the movable member which is fixed with respect to the holder. On the other hand, the movable member may be moved relatively to the holder when lancing, thereby breaking the sealing.

The attachment according to the present invention further comprises, preferably, a cap co-holding the analyzing implement with the movable member. In this case, removal of the cap leaves the analyzing implement held by the movable member.

The movable member includes for example, first holding means for holding the analyzing implement whereas the cap includes second holding means for holding the analyzing implement. In this case, the first holding means has a greater holding force for holding the analyzing implement than the second holding means.

The first holding means has a plurality of hook-like engagers. The second holding means includes for example, an engager having a diameter grater than that of the though hole, for insertion through the through hole.

The analyzing implement includes for example, a substrate, and a first and a second electrodes formed on the substrate. In this case, preferably, the analyzing implement is held by the movable member, with part of the first and the second electrodes extending sideways of the movable member.

The lancing member is preferably integral with the holder via a weak portion. In this case, the lancing member moves relatively to the holder upon a longitudinal load onto the lancing member.

A second aspect of the present invention provides a method of making an attachment for body fluid sampling device, comprising: a sealing step of sealing a lancing needle held by an attachment main body; a sterilizing step of sterilizing the attachment main body which holds the lancing needle; and an analyzing implement mounting step of mounting an analyzing implement in the sterilized attachment main body.

The analyzing implement mounting step is preferably performed by attaching a cap which holds the analyzing implement to the attachment main body. The cap may not be used of course, to have the analyzing implement held by the attachment main body.

The attachment main body includes an inner space communicating with outside via an opening. In this case, the sealing step is performed by sealing the opening with a seal.

In the sealing step, the seal is fixed to the attachment main body by ultrasonic fusing.

The sealing step may include formation of a holder holding the lancing needle, and integration thereafter of the holder with a movable member which has holding means for holding the analyzing implement and is movable back and forth relatively to the holder. Alternatively, the analyzing implement may be held by the movable member, and the mounting of the analyzing implement in the attachment main body may be performed by attaching the movable member to the holder. In this case, the integration of the holder with the movable member does not constitute part of the sealing step, and is performed as a separate step from the sealing step.

BRIEF DESCRIPTION OF THE DRAWINGS

FIGS. 2A and 2B are longitudinal sections of the attachment in FIG. 1.

FIGS. 7A through 7C are sectional views for describing a method of making the attachment in FIG. 1.

FIGS. 10A through 10D are sectional views for describing a lancing action by the body fluid sampling device and the attachment.

BEST MODE FOR CARRYING OUT THE INVENTION

Figure 1:
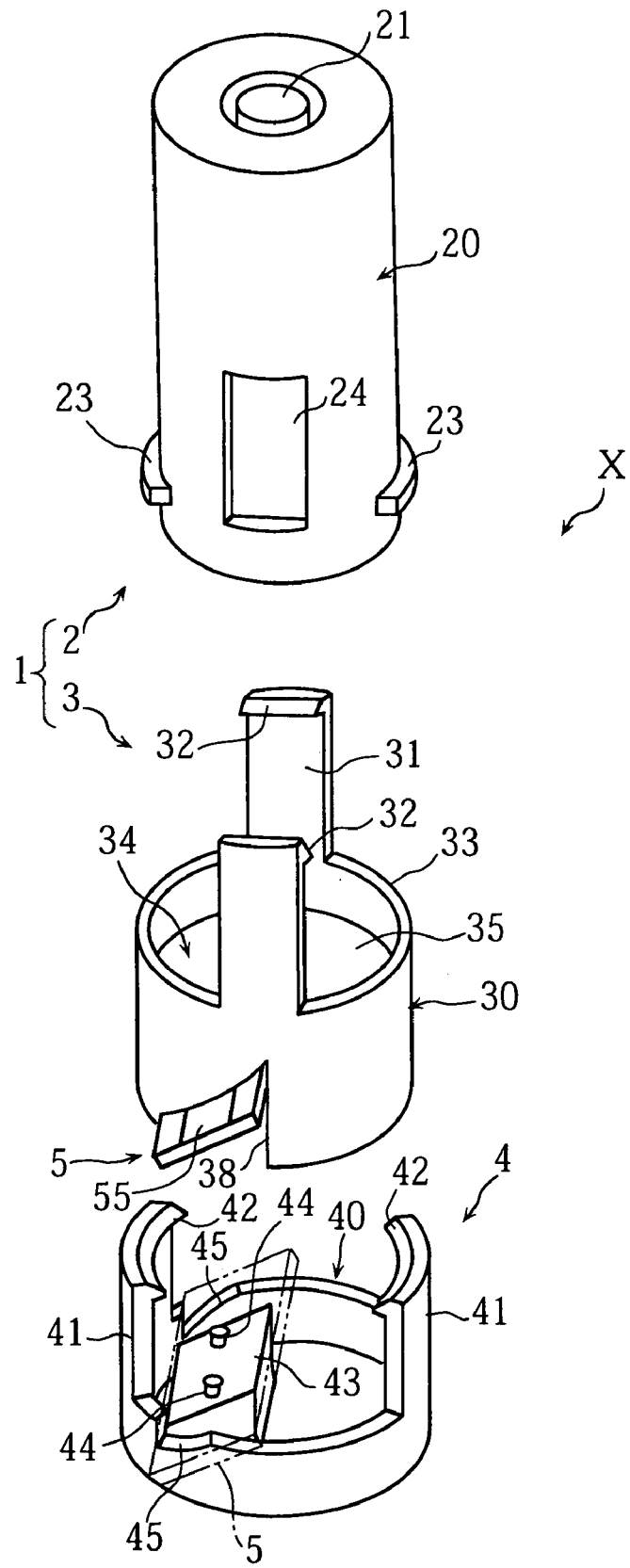
FIG. 1 is an exploded perspective view of an attachment according to the present invention.

Hereinafter, an example of the attachment for body fluid sampling device according the present invention will be described with reference to attached drawings. FIG. 1 is an exploded perspective view of an attachment according to the present invention. FIG. 2 shows longitudinal sections of the attachment in FIG. 1.

As shown in FIG. 1 and FIG. 2, an attachment X includes: an attachment main body 1 having a holder 2 and a movable member 3; a cap 4; a lancing member 21; and a biosensor 5.

The holder 2 includes a tubular main body 20 which provides an inner space 22. The main body 20 holds the lancing member 21. The main body 20 has a lower circumferential surface formed with a pair of flanges 23 and a pair of guide recesses 24. The flanges 23 are circumferential whilst the guide recesses 24 are longitudinal. The inner space 22 communicates with the outside via an opening 25. The opening 25 is sealed with a seal 26.

The lancing member 21, on the other hand, includes a holder 27 and a lancing needle 28. The lancing needle 28 has its tip extending from the holder 27. The lancing member 21 further includes a brim 29 extending radially outward. The brim 29 is provided all around the lancing member 21. The lancing member 21 is integral with the main body 20 via the brim 29. The connection between the brim 29 and the main body 20 is provided by a thin wall, so that when the lancing member 21 comes under a load exceeding a predetermined level, the lancing member 21 detaches from the main body 20. Since the brim 29 is all around the lancing member 21 and the opening 25 of the inner space 22 is sealed, the lancing needle 28 is sealed in. Alternatively however, the lancing member 21 may be formed as a separate member from the main body 20.

Figure 3:
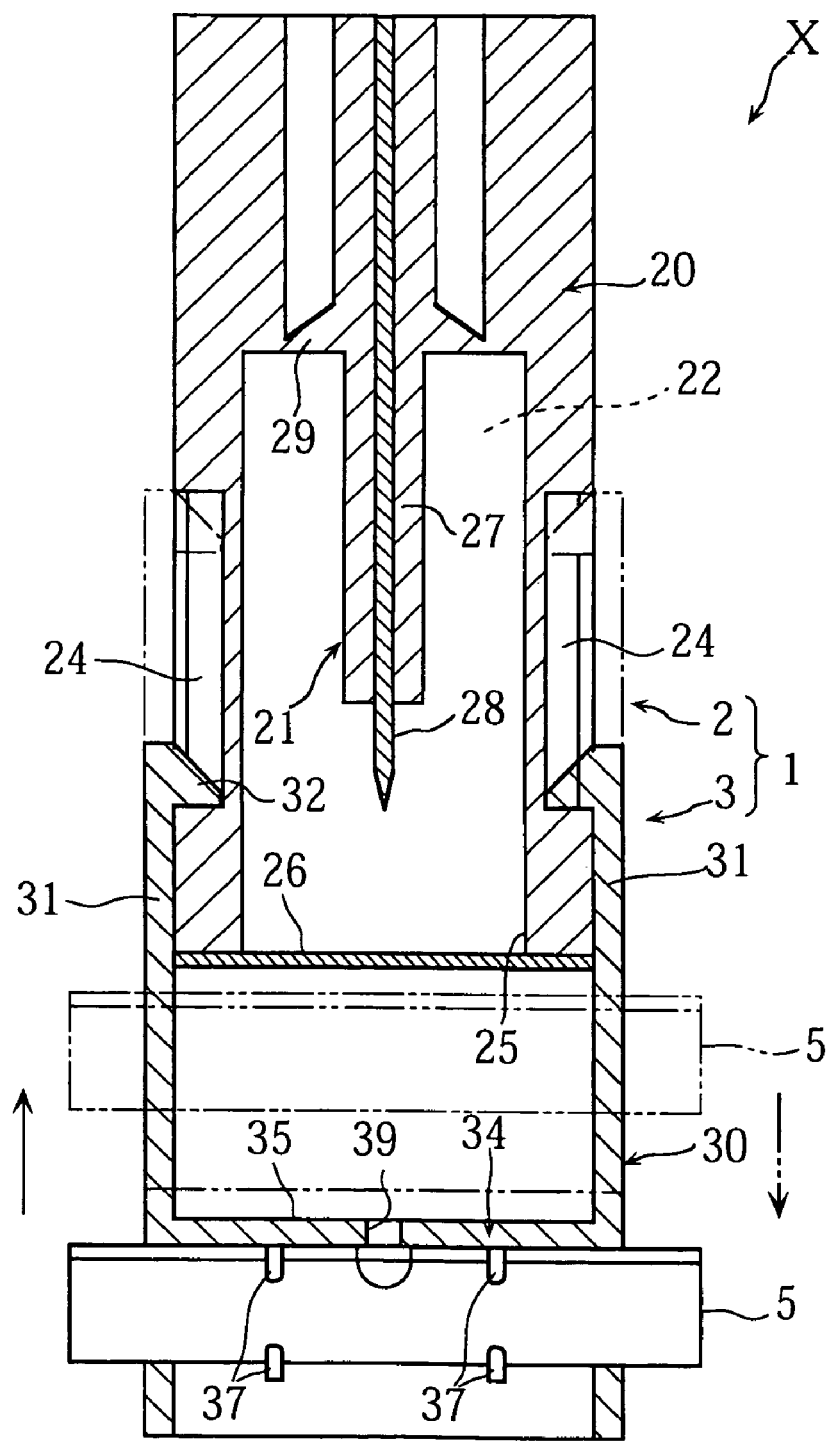
FIG. 3 is a sectional view for describing how a movable member works in the attachment in FIG. 1.

The movable member 3 includes a main body 30, and a pair of engaging tabs 31 extending upward therefrom. The engaging tabs 31 mate with the guiding recesses 24 of the holder 2. The engaging tabs 31 each have an upper tip formed with an engaging pawl 32. The engaging pawl 32 engages with the corresponding one of the guiding recesses 24, and is movable therein. As a result, as shown in FIG. 3, the movable member 3 can move relatively to the holder 2 in vertical directions.

As shown in. FIG. 1 and FIG. 2, the main body 30 of the movable member 3 includes a tubular portion 33 and a sensor attaching seat 34. The sensor attaching seat 34 has a flat upper surface 35. When the holder 2 is approached most closely by the movable member 3, the holder 2 has its lower end contacting to the upper surface 35 of the sensor attaching seat 34 via the seal 26.

Figure 4A:
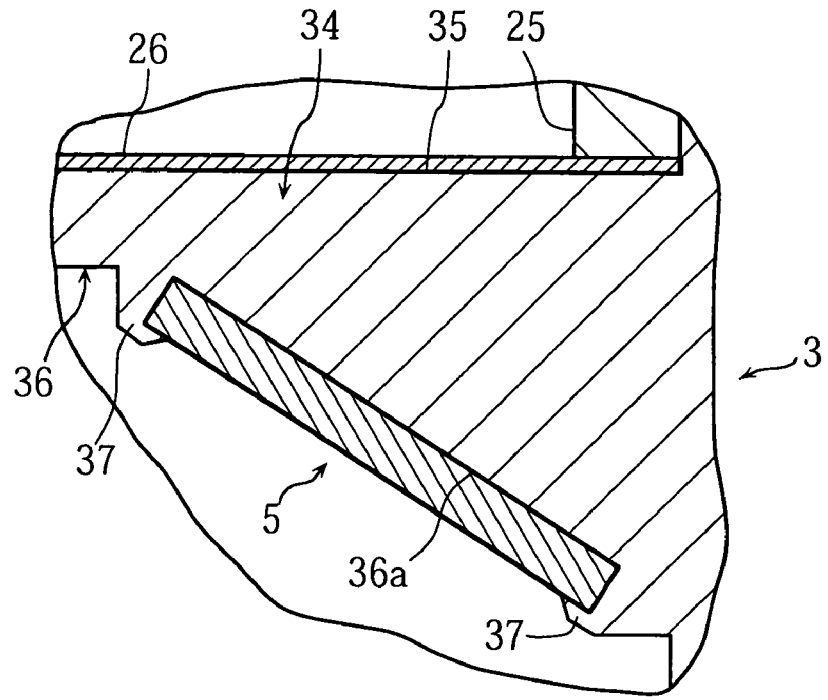
FIGS. 4A and 4B are enlarged views of primary portions of the attachment in FIG. 1.

The sensor attaching seat 34 has a lower surface 36 formed with a mounting surface 36a to which a sensor 5 to be described later (See FIG. 5 and FIG. 6) is attached. The mounting surface 36a is slanted with respect to the upper surface 35 of the sensor attaching seat 34. As shown in FIG. 3 and FIG. 4A, the mounting surface 36a is formed with two pairs of engagers 37. The engagers 37 hold the biosensor 5 to the movable member 3. As shown clearly in FIG. 1 and FIG. 2B, the biosensor 5 has its two ends extending from the movable member 3 when attached to the mounting surface 36a. Correspondingly, the movable member 3 is formed with cutouts 38 as shown clearly in FIG. 1.

The sensor attaching seat 34 has a center region formed with a through hole 39. When the lancing member 21 moves down, the lancing needle 28 goes through the through hole 39, with the tip of the lancing needle 28 projecting out of the lower surface 36 of the sensor attaching seat 34. The through hole 39 has a diameter smaller than that of the holder 27. Thus, when the lancing member 21 moves down, the tip of the holder 27 interferes with the upper surface 35 of the sensor attaching seat 34 via the seal 26, limiting the movement of the lancing member 21. As a result, the amount of projection of the lancing needle 28 is constant.

As shown in FIG. 1 and FIG. 2, the cap 4 includes a tubular main body 40 with an open upper end, and a pair of engaging tabs 41 extending upward from the main body 40. The engaging tabs 41 each have a tip formed with an engager 42. As clearly shown in FIG. 2A, the engagers 42 are mated with the flanges 23 of the holder 2. By engaging the engagers 42 with the flanges 23, the cap 4 is attached to the attachment main body 1 to cover the movable member 3. In this sate, as clearly shown in FIG. 2B, the distance between the holder 2 and the movable member 3 is the smallest.

As shown in FIG. 1 and FIG. 2A, the main body 40 of the cap 4 has a bottom surface from which a pedestal 43 stands out upwardly. The pedestal 43 holds the biosensor 5. As clearly shown in FIG. 4B, the pedestal 43 has an upper surface 43a which is slanted at an angle matched to the mounting surface 36a of the movable member 3. Also, as shown in this figure and in FIG. 1 the upper surface 43a of the pedestal 43 is formed with a pair of engagers 44. As clearly shown in FIG. 4B, these engagers 44 and the through holes in the biosensor 5 (See FIG. 5 and FIG. 6.) secure the biosensor 5 on the pedestal 43. The biosensor 5 is also held by the movable member 3, and the holding force by the cap 4 is smaller than the holding force by the movable member 3. Therefore, when the cap 4 is removed from the attachment main body 1, the biosensor 5 remains held by the movable member 3, and the biosensor 5 is removed from the cap 4. As shown clearly in FIG. 1 and FIG. 2B, the biosensor 5 has its two ends extending out of the cap 4 when held on the pedestal 43. Corresponding to this, the cap 4 is formed with cutouts 45 as clearly shown in FIG. 1.

Figure 5:
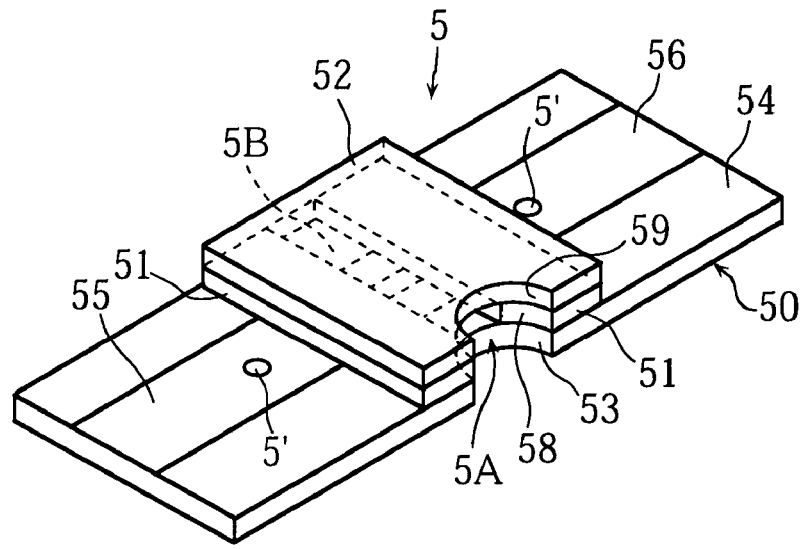
FIG. 5 is an overall perspective view of a biosensor used in the attachment in FIG. 1.
Figure 6:
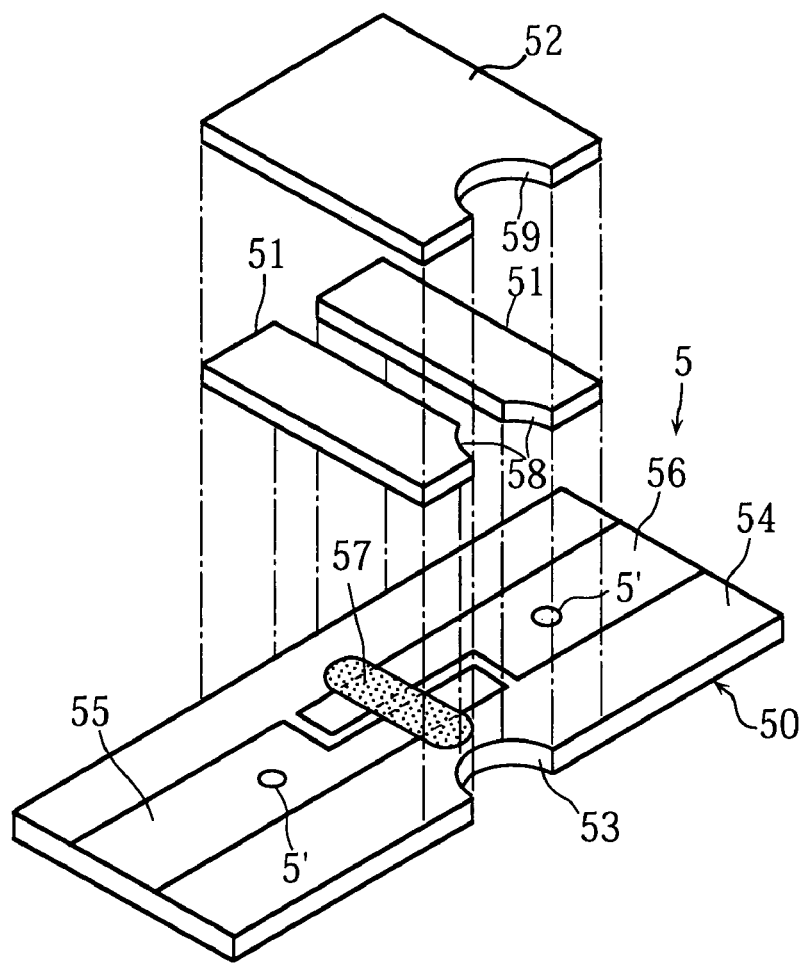
FIG. 6 is an exploded perspective view of the biosensor in FIG. 5.

A biosensor 5 has, for example, a structure shown in FIG. 5 and FIG. 6. This biosensor 5 includes a substrate 50, a pair of spacers 51 and a cover 52.

The substrate 50 is made of an insulating member, and in a rectangular shape. The substrate 50 is formed with a cutout 53. The substrate 50 has a surface 54 formed with a reaction electrode 55, a pairing electrode 56 and a reagent layer 57. The reaction electrode 55 and the pairing electrode 56 each extend from a shorter edge of the substrate 50 toward a center region of the substrate 50, with a portion at the center region being narrower. The reagent layer 57 is like a belt laid across the reaction electrode 55 and the pairing electrode 56. The reagent layer 57 is solid, containing an oxidation-reduction enzyme provided by glucose dehydrogenase for example, and an electron transfer material provided by potassium ferricyanide for example.

The spacers 51 are rectangular, with a length equal to the width of the substrate 50, and with a corner formed with an arcuate cutout 58. These spacers 51 are respectively placed on two sides of the reagent layer 57, in parallel to each other and spaced by a distance equal to the width of the reagent layer 57.

The cover 52 is rectangular, with a length equal to the width of the substrate 50, with one of the ends formed with an arcuate cutout 59. The cover 52 has the cutout 59 aligned with the cutout 53 of the substrate 50, and is fixed on the pair of spacers 51 to bridge these spacers 51.

According to the biosensor 5, each of the substrate 50, the spacers 51 and the cover 52 is formed with a cutout 53, 58 or 59. These cutouts form a recess 5A, which is like a halved tube, through the thickness and opening in a direction along the width of the substrate 50. As will be described later, the recess 5A serves as a receiver of blood bled from the skin. Further, according to the biosensor 5, the substrate 50, the spacers 51 and the cover 52 collectively form a channel 5B across the width of the substrate 50. The channel 5B has an end communicating with the outside via the recess 5A, and another end communicating with the outside. Therefore, when the blood is introduced from the recess 5A, the capillarity makes the blood move through the channel toward the other end. Since there is the reagent layer 57 in the channel 5B, the blood moving through the channel 5B dissolves the reagent layer 57. During this, glucose contained in the blood is oxidized in an enzyme reaction, and electrons released in this reaction reduce the electron transfer material.

The attachment X as described above can be manufactured in the steps to be described here below. It should be noted that formation is already made for a holder 2, a movable member 3 and a cap 4, by means of resin injection molding. Note further that the holder 2 is provided with a lancing member 21 integrally therewith, and a biosensor 5 is already prepared.

First, as shown in FIG. 7A, the opening 25 of the holder 2 is sealed with a seal 26. This achieves that the lancing needle 28 is held under a sealed condition. The seal 26 can be provided by a metal foil such as aluminum foil or a resin sheet. The seal 26 is fixed to the holder 2 by ultrasonic fusing for example. Then, with the lancing needle 28 held under the sealed condition, the lancing needle 28 is sterilized together with the holder 2. The sterilization can be performed by gamma ray radiation for example.

Next, as shown in FIG. 7B, the movable member 3 is attached to the holder 2, to make an attachment main body 1. The attaching of the movable member 3 is achieved by engaging the engaging pawls 32 of the movable member 3 with the guiding recesses 24 of the holder 2. At this stage, the biosensor 5 is not yet fixed to the movable member 3.

Figure 4B:
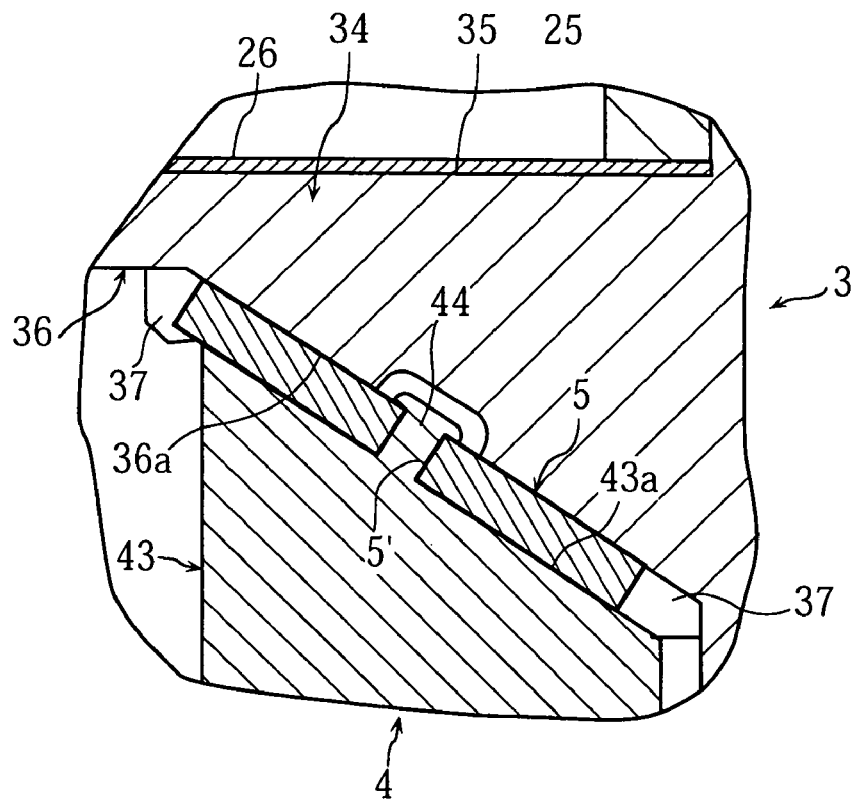

Then, as shown in FIG. 7C, the cap 4 which holds the biosensor 5 is attached to the attachment main body 1, whereby an attachment X as shown in FIG. 2 and other drawings is completed. It should be noted that the attaching of the biosensor 5 to the cap 4 is achieved as shown in FIG. 4B; i.e. the engagers 44 of the cap 4 are inserted through respective through holes 5' and snapped around the through holes. On the other hand, the cap 4 is attached, as shown in FIG. 7C; i.e. the engagers 42 of the cap 4 are engaged with the flanges 23 of the holder 2. Once the cap 4 has been attached to the attachment main body 1, as clearly shown in FIG. 2B, the tip of the holder 2 contacts the upper surface 35 of the sensor attaching seat 34 of the movable member 3 via the seal 26, whereas the tip of the movable member 3 contacts the bottom surface of the main body 40 of the cap 4. In other words, the holder 2 and the cap 4 sandwich the movable member 3. As a result, the biosensor 5 is pressed against the mounting surface 36a of the movable member 3, and as shown in FIG. 4A, the biosensor 5 is held in the engagers 37 of the movable member 3.

According to a method such as the above, when making the attachment X, the lancing needle 28 is sterilized separately from the biosensor 5. Therefore, the sterilization process does not alter or destroy the oxidation-reduction enzyme, nor chemically reduce the electron transfer material contained in the reagent layer 57 of the biosensor 5. Therefore, measuring accuracy is not affected by the sterilization process of the lancing needle 28.

Since the lancing needle 28 is sterilized under a sealed condition, the lancing needle 28 is protected from contamination by fungi for example until the sealing is broken (till the time of use).

The biosensor 2 is held against the movable member 3 can be achieved by a simple operation such as attaching the cap 4 onto the attachment main body 1, resulting in good operability.

Figure 8:
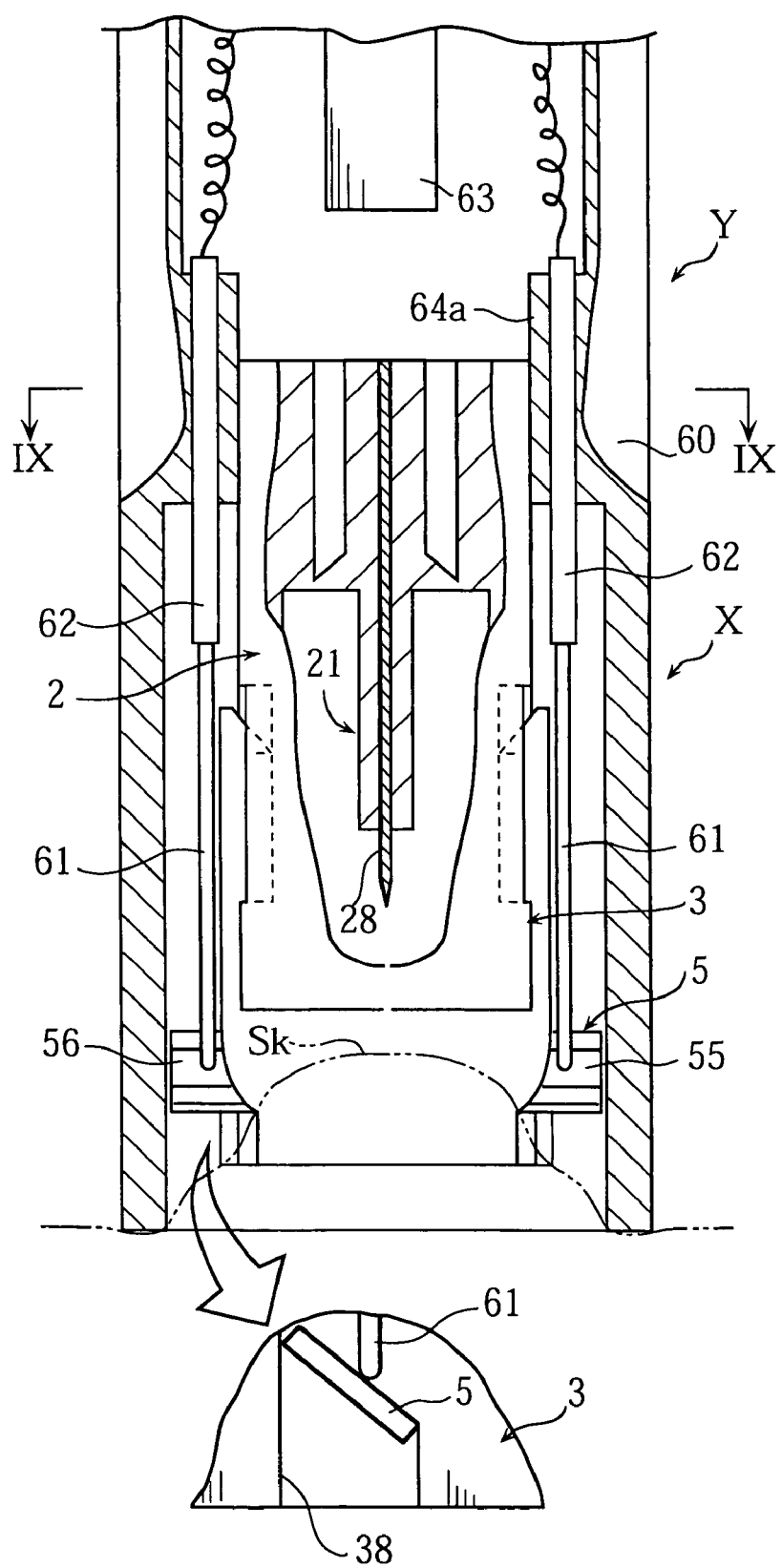
FIG. 8 is a fragmentary sectional view, showing a primary portion of the attachment in FIG. 1 as attached to a body fluid sampling device.
Figure 9:
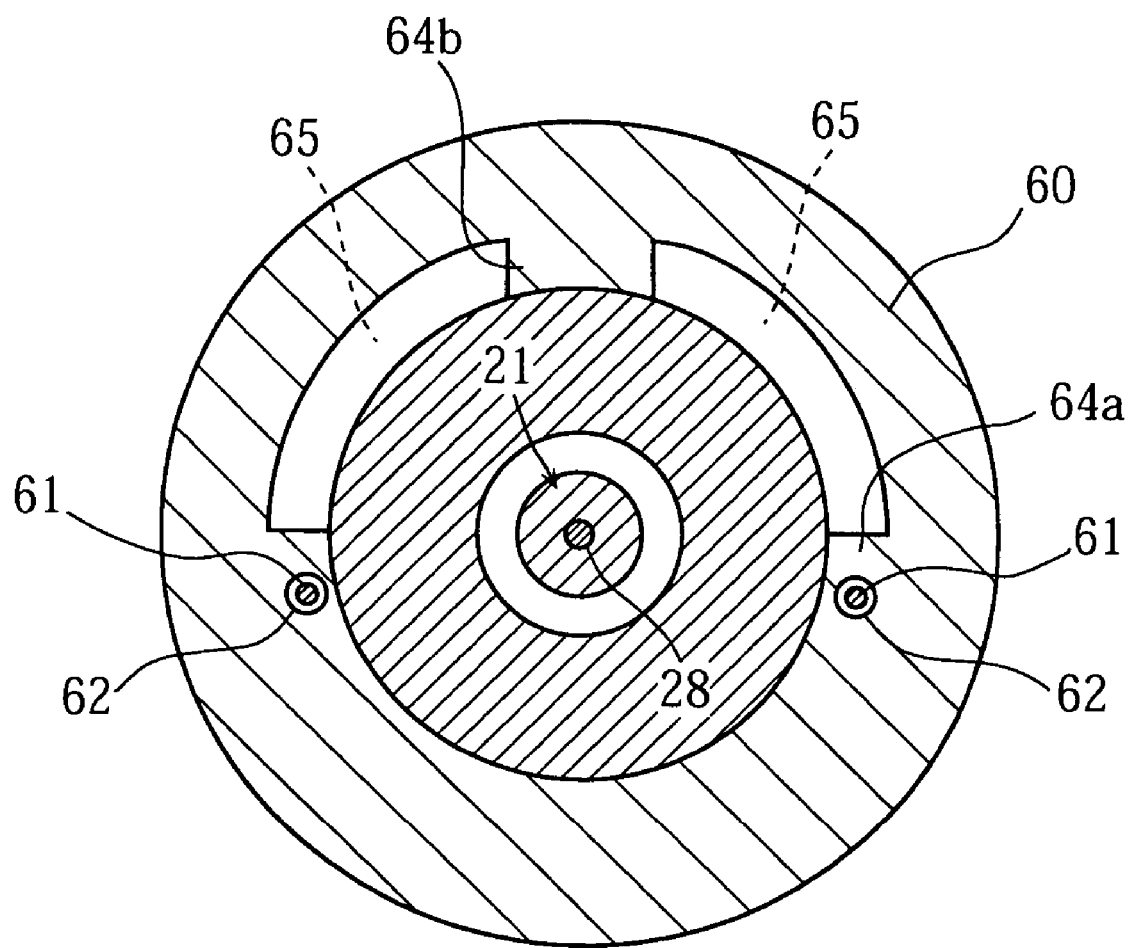
FIG. 9 is a sectional view taken in lines IX-IX in FIG. 8.

As shown in FIG. 8 and FIG. 9, the attachment X is used as attached to a tip 60 of a body fluid sampling device Y. As fitted to the tip 60 of the body fluid sampling device Y, the holder 3 of the attachment X is contacted to the flanges 64a, 64b on an inner surface of the tip 60 of the body fluid sampling device Y. Since the mounting of the attachment X is made by fitting the holder 2 onto the flanges 64a, 64b of the body fluid sampling device Y, there is a gap between the movable member 3 and the tip 60, which allows relative vertical movement of the movable member 3 with respect to the tip of the body fluid sampling device Y. As will be expected from FIG. 8, when the movable member 3 comes to its lowest position, the tip of the movable member 3 projects out of the tip of the body fluid sampling device Y, whereas the movable member 3 is completely housed into the tip 60 of the body fluid sampling device Y when the movable member 3 comes to its highest position.

When lancing operation is made, the cap 4 is removed. The cap 4 may be removed after the attachment X is attached to the body fluid sampling device Y, or the cap 4 may be removed before the attachment main body 1 is attached to the body fluid sampling device Y. In any case, the cap can remain on the movable member 3 till the moment of lancing operation, and thus the biosensor 5 can be protected by the cap 4 till the moment of lancing operation.

The body fluid sampling device Y includes a pair of connector pins 61 extending downward. These connector pins 61 are held in respective holders 62, and are urged downward for vertical movement, by respective coils (not illustrated) placed in the holders 62. As shown in FIG. 8 and FIG. 9, the holders 62 are fixed at the flange 64a of the body fluid sampling device Y. This flange 64a is also used for fitting the holder 2 of the attachment X. Once the attachment X (the holder 2) is fitted to the body fluid sampling device Y, there is a gap 65 between the attachment X (the holder 2) and an inner surface of the tip 60 of the body fluid sampling device Y. The gap 65 communicates with the outside. The gap 65 also communicates with the inside of the movable member 3 via a cutout 38. Further, once the attachment X is attached to the body fluid sampling device Y, the connecting pins 61 make contact with the reaction electrode 55 and the pairing electrode 56 of the biosensor 5. Since the connecting pins 61 are urged downward for vertical movement, when the movable member 3 moves vertically, connector pins 61 also move vertically, maintaining connections with the reaction electrode 55 and the pairing electrode 56.

The body fluid sampling device Y incorporates a pusher 63 which can be moved downward. The pusher 63 can be moved in different method: For example, the pusher 63 may be latched under a downward urge so that the latch may be released by pushing a button. The urging of the pusher 63 can be provided by an elastic member such as a coil spring and foamed resin. Of course the pusher 63 may be moved by an electromagnetic method: Specifically, the pusher 63 or a member to move therewith is provided with a magnet, and an electric magnet is faced to the magnet. According to this arrangement, pressing of the button causes a repelling force between the magnet and the electric magnet to move the pusher 63 downward. Alternatively, a suction pump may be used to move the pusher 63 pneumatically.

When lancing, as shown in FIG. 10A, the tip of the body fluid sampling device Y is contacted onto a lancing point or skin surface Sk. In this step, the tip of the body fluid sampling device Y may be rubbed against or pressed strongly onto the skin surface Sk in order to promote bleeding upon lancing. Of course the gap 65 and the cutouts 38 may be used to generate a partial vacuum in the movable member 3. During this, if the skin surface Sk is sucked upward, the skin surface Sk contacts the biosensor 5 (See FIG. 10B). Since the movable member 3 is movable relatively to the holder 2, the movable member 3 moves vertically in accordance with the bulge of the skin surface Sk while maintaining contact with the skin surface Sk. As a result, bleeding can be reliably promoted according to the attachment X, differing from cases where the biosensor is totally immovable.

When lancing, the pusher 63 provides a pressing force to the lancing member 21, causing the lancing member 21 to move downward. When the pusher 63 moves downward, as shown in FIG. 10B, the pusher 63 interferes with the upper end of the lancing member 21, giving a pressing force to the lancing member 21. This pressing force cuts the brim 29 of the lancing member 21 off the main body 20, moving the lancing member 21 downward, independently from the main body 20. As shown in FIG. 10C, the lancing needle 28 breaks the seal 26, and moves through the through hole 39 of the movable member 3. Then, as shown in FIG. 10D, the lancing needle 28 sticks into the lancing point, causing the body fluid to bleed from the skin surface Sk.

Figure 11:
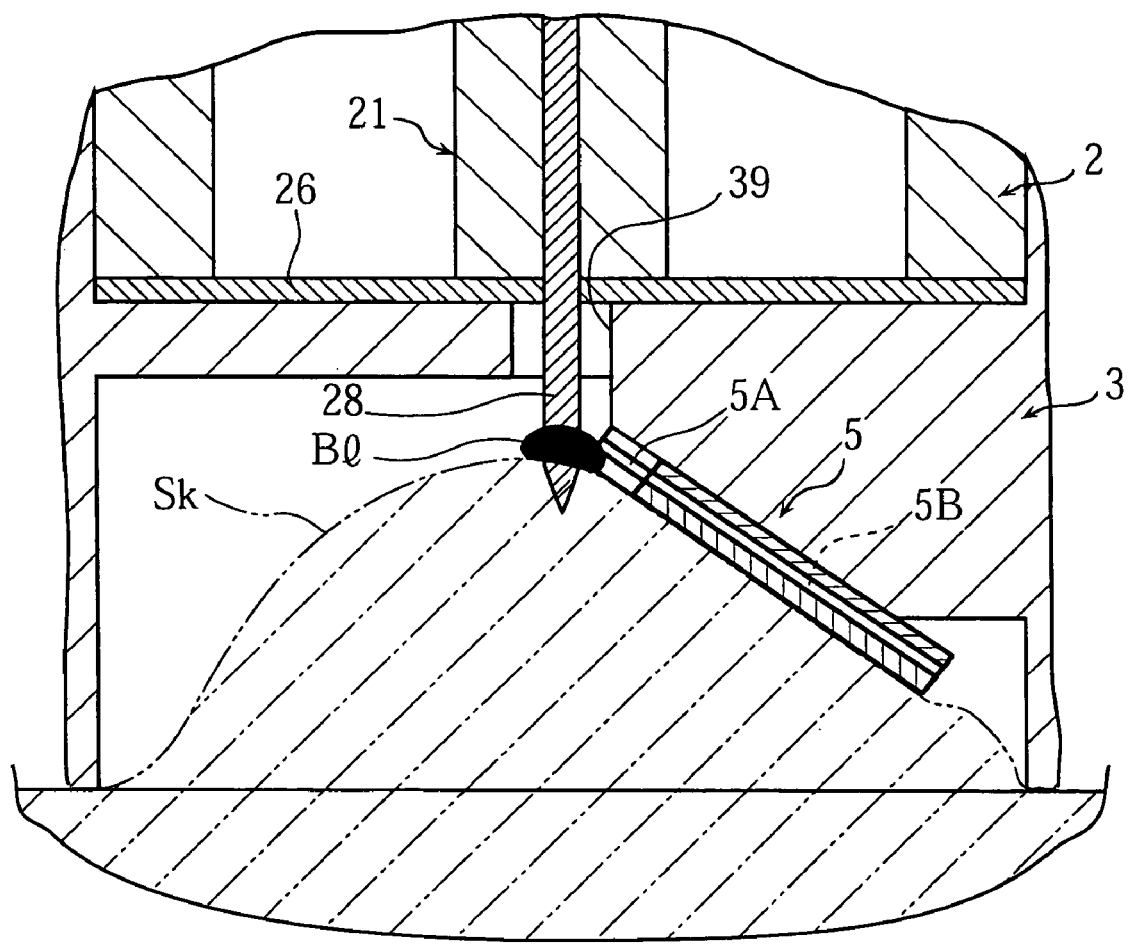
FIG. 11 is an enlarged view, showing a primary portion of the body fluid sampling device under a lancing state.
Figure 12:
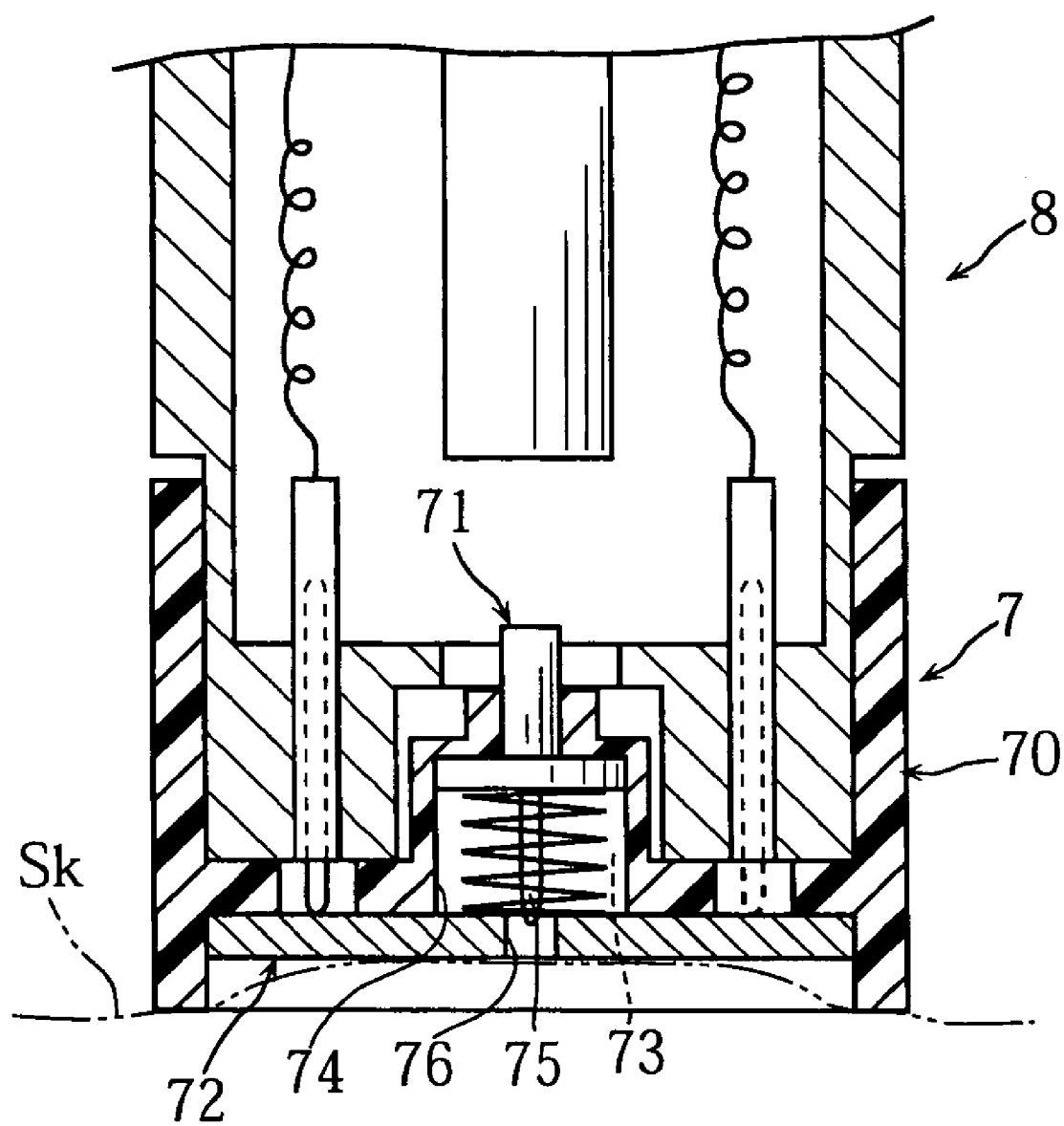
FIG. 12 is a sectional view showing a primary portion of a blood sugar level tester incorporating a conventional attachment.

As shown in FIG. 11, blood B1 from the skin surface Sk collects in the recess 5A of the biosensor 5, and then flows to the channel 5B (See FIG. 8). In the reagent layer 57 (See FIG. 6), the oxidation-reduction enzyme promotes an oxidation-reduction reaction between blood glucose and the electron transfer material, in which the electron transfer material is chemically reduced. The reagent layer 57 is applied with a voltage via the connecting pins 61 (See FIG. 8), the reaction electrode 55 and the pairing electrode 56 (See FIG. 5 and FIG. 6). The voltage oxidizes the electron transfer material. Concomitantly, the body fluid sampling device Y makes measurements via the connector pins (See FIG. 8), of the electrons released during the oxidation process of the electron transfer material, in the form of oxidation current. Based on this oxidation current, a blood glucose level is calculated.

The present invention is not limited to the embodiment described here above. For example, the technical idea of the present invention is applicable generally to attachments for concentration level measuring devices which perform lancing and measuring simultaneously. For example therefore, the technical idea of the present invention is applicable to cholesterol level testers and lactic acid level testers which use enzyme reactions. Further, the technical idea of the present invention is applicable to attachments for lancing devices which are intended solely for lancing operation.

Different designs may be used for giving a pressing force to the lancing member. For example, the attachment may be integrated with a moving member serving as a pusher, and the moving member may be moved toward the skin surface so that the skin surface is hit by the attachment and an impact from the hit serves as the pressing force onto the lancing member to achieve the lancing.

A cap may not necessarily be used for assembling the biosensor into the movable member.

The invention claimed is:

1. An attachment for mounting to a tip of a body fluid sampling device that includes a pusher for imparting a lancing force, the attachment comprising:
    a first main body holding a lancing member including a lancing needle;
    a second main body provided separately from the first main body and holding an analyzing implement for obtaining information on a target component in body fluid, the second main body holding the analyzing implement without holding the lancing member; and
    a cap removably mounted to the second main body for holding the analyzing implement between the second main body and the cap;
    wherein the second main body is mounted to the first main body, the second main body being movable together with the analyzing implement relative to the first main body longitudinally of the lancing needle even while the second main body is kept mounted to the first main body and held in contact with a sampling target,
    wherein the analyzing implement is held by the second main body at a position radially offset relative to the lancing needle for avoiding contact with the lancing needle upon lancing,
    wherein removal of the cap leaves the analyzing implement held by the second main body,
    wherein the second main body includes a first seat for holding the analyzing implement,
    wherein the cap includes a second seat for holding the analyzing implement, the analyzing implement being sandwiched between the first seat and the second seat, and
    wherein the first seat has a greater holding force for holding the analyzing implement than the second seat.

2. The attachment according to claim 1, wherein
    the first main body includes a holder for holding the lancing member,
    the first main body having an inner space for movement of the lancing member,
    the lancing needle being held sealed in the inner space.

3. The attachment according to claim 2, wherein
    the holder includes an opening for the inner space to communicate with outside,
    the inner space being sealed by a seal on the opening.

4. The attachment according to claim 1, wherein the first seat has a plurality of hook-like engagers.

5. The attachment according to claim 1 wherein
    the analyzing implement includes a through hole,
    the second seat is provided with an engager for insertion through the through hole, the engager having a diameter greater than that of the though hole.

6. The attachment according to claim 1, wherein the analyzing implement includes a substrate, a first electrode formed on the substrate, and a second electrodes formed on the substrate, the analyzing implement being held by the second main body with part of the first and second electrodes extending sideways of the second main body.

7. The attachment according to claim 2, wherein
    the lancing member is integral with the holder via a weak portion,
    the lancing member moves relatively to the holder upon a longitudinal load onto the lancing member.

8. The attachment according to claim 1, wherein one of the first main body and the second main body is formed with a guide groove extending longitudinally of the lancing needle, the other of the first main body and the second main body being provided with an engaging element slidably engaging in the guide groove.

* * * * *